(12) United States Patent
Morikawa et al.

(10) Patent No.: US 9,162,219 B2
(45) Date of Patent: Oct. 20, 2015

(54) FENTON REACTION CATALYST PRODUCED USING REDUCING ORGANIC SUBSTANCE AS RAW MATERIAL

(75) Inventors: Claudio Kendi Morikawa, Tsu (JP); Makoto Shinohara, Tsu (JP)

(73) Assignee: INCORPORATED ADMINISTRATIVE AGENCY, NATIONAL AGRICULTURE AND FOOD RESEARCH ORGANIZATION, Tsukuba-Shi, Ibaraki (JP)

( * ) Notice: Subject to any disclaimer, the term of this patent is extended or adjusted under 35 U.S.C. 154(b) by 58 days.

(21) Appl. No.: 14/110,528
(22) PCT Filed: Apr. 6, 2012
(86) PCT No.: PCT/JP2012/059453
§ 371 (c)(1), (2), (4) Date: Oct. 8, 2013
(87) PCT Pub. No.: WO2012/157365
PCT Pub. Date: Nov. 22, 2012

(65) Prior Publication Data
US 2014/0031196 A1    Jan. 30, 2014

(30) Foreign Application Priority Data
May 17, 2011 (JP) ................................ 2011-110173

(51) Int. Cl.
*B01J 23/745* (2006.01)
*B01J 31/22* (2006.01)
(Continued)

(52) U.S. Cl.
CPC ................. *B01J 31/04* (2013.01); *A01N 59/00* (2013.01); *A01N 59/16* (2013.01); *A61L 2/0088* (2013.01);
(Continued)

(58) Field of Classification Search
CPC ...... B01J 23/745; B01J 31/0202; B01J 31/22; C02F 1/722

USPC .................. 502/170, 338; 530/300; 588/300; 252/700; 23/293 R
IPC ........ B01J 23/745,31/0202, 31/22; C02F 1/722
See application file for complete search history.

(56) References Cited

U.S. PATENT DOCUMENTS

| 2,535,627 A | 12/1950 | Earp-Thomas |
| 3,706,545 A | 12/1972 | Gray et al. |

(Continued)

FOREIGN PATENT DOCUMENTS

| CA | 1032823 A1 | 6/1978 |
| CN | 101507457 A | 8/2009 |

(Continued)

OTHER PUBLICATIONS

"Enhanced chemical oxidation of aromatic hydrocarbons in soil systems," Namgoo Kang et al. Chemosphere 61 (2005), pp. 909-922.*
(Continued)

*Primary Examiner* — Patricia L Hailey
(74) *Attorney, Agent, or Firm* — Holtz, Holtz, Goodman & Chick PC

(57) ABSTRACT

To develop a Fenton reaction catalyst that can maintain divalent iron stably for a long period of time, can utilize trivalent iron or metallic iron, which is an inexpensive iron-supplying source, by converting into divalent iron, and is harmless to the human body and the environment, provided is a Fenton reaction catalyst, including, as an active component, a reaction product obtained by mixing a specific reducing organic substance (e.g., ascorbic acid, a polyphenol-containing plant component, or a plant dry distillation liquid component) with an iron-supplying source at a predetermined ratio in the presence of water. Also provided are a sterilization method, a pollutant degradation method, and a luminescence method based on chemiluminescence, which involve using the Fenton reaction catalyst.

8 Claims, 5 Drawing Sheets

(51) Int. Cl.
*B01J 31/04* (2006.01)
*B09C 1/08* (2006.01)
*A01N 59/00* (2006.01)
*A61L 2/00* (2006.01)
*A61L 2/18* (2006.01)
*A61L 2/22* (2006.01)
*B01J 31/02* (2006.01)
*F21K 2/06* (2006.01)
*A01N 59/16* (2006.01)
*B01J 27/10* (2006.01)
*B01J 27/128* (2006.01)
*C02F 1/72* (2006.01)

(52) U.S. Cl.
CPC . *A61L 2/186* (2013.01); *A61L 2/22* (2013.01); *B01J 27/10* (2013.01); *B01J 27/128* (2013.01); *B01J 31/0202* (2013.01); *B09C 1/08* (2013.01); *F21K 2/06* (2013.01); *C02F 1/72* (2013.01); *C02F 2303/04* (2013.01); *C02F 2305/026* (2013.01); *Y02W 10/37* (2013.01)

(56) References Cited

U.S. PATENT DOCUMENTS

| | | | |
|---|---|---|---|
| 4,006,263 A | | 2/1977 | Klug et al. |
| 4,528,200 A | | 7/1985 | Coleman |
| 5,741,427 A | * | 4/1998 | Watts et al. ............... 210/747.8 |
| 6,319,328 B1 | * | 11/2001 | Greenberg et al. ............... 134/2 |
| 6,488,732 B2 | | 12/2002 | Scanlan |
| 7,662,294 B1 | * | 2/2010 | Cox, Jr. ............... 210/759 |
| 2002/0064567 A1 | | 5/2002 | Jassim et al. |
| 2004/0134857 A1 | * | 7/2004 | Huling et al. ............... 210/668 |
| 2005/0031761 A1 | | 2/2005 | Brucker et al. |
| 2006/0175266 A1 | * | 8/2006 | Rima et al. ............... 210/764 |
| 2009/0188290 A1 | | 7/2009 | Marler |
| 2010/0068297 A1 | | 3/2010 | Naughton |
| 2011/0023566 A1 | | 2/2011 | Lodwig et al. |
| 2012/0285891 A1 | * | 11/2012 | Lundy ............... 210/668 |
| 2013/0008215 A1 | | 1/2013 | Morikawa et al. |
| 2013/0017270 A1 | | 1/2013 | Morikawa et al. |
| 2014/0127078 A1 | | 5/2014 | Morikawa et al. |
| 2014/0200335 A1 | * | 7/2014 | Olkowski et al. ............ 530/500 |

FOREIGN PATENT DOCUMENTS

| | | | |
|---|---|---|---|
| DE | 19628575 A1 | | 1/1998 |
| DE | 19700368 A1 | | 7/1998 |
| EP | 896792 A1 | | 2/1999 |
| EP | 2554042 A1 | | 2/2013 |
| JP | 58156539 A | | 9/1983 |
| JP | 61-059248 A | | 3/1986 |
| JP | 04114985 A | | 4/1992 |
| JP | 4-198111 A | | 7/1992 |
| JP | 06-106173 A | | 4/1994 |
| JP | 9-136807 A | | 5/1997 |
| JP | 2002-282874 A | | 10/2002 |
| JP | 2004-249258 A | | 9/2004 |
| JP | 2004-250390 A | | 9/2004 |
| JP | 2005087216 A | | 4/2005 |
| JP | 2007-125521 A | | 5/2007 |
| JP | 2007-195546 A | | 8/2007 |
| JP | 2009-062350 A | | 3/2009 |
| JP | 2009-073772 A | | 4/2009 |
| JP | 2009-269843 A | | 11/2009 |
| JP | 2011-212518 A | | 10/2011 |
| PT | 0501652 | * | 12/2006 |
| WO | 2004089092 A1 | | 10/2004 |
| WO | WO 2007/013219 A1 | | 2/2007 |
| WO | 2009140694 A2 | | 11/2009 |
| WO | 2010116379 A1 | | 10/2010 |

OTHER PUBLICATIONS

"Decomposition of 2-chlorophenol employing goethite as Fent catalyst. I. Proposal of a feasible, combined reaction scheme of heterogeneous and homogeneous reactions," Guadalupe B. Ortiz de la Plata et al. Applied Catalysis B: Environmental 95 (2010), pp. 1-13.*

Extended European Search Report dated Nov. 20, 2014 issued in counterpart European Application No. 12786456.9.

Stuart C. Blanchard; "Electron Paramagnetic Resonance Spectrum of a Sea Shell. Mytilus edulis"; The Journal of Physical Chemistry, vol. 80, No. 12, 1976, 1362-1367.

Babich, et al., "Mediation of the in vitro cytotoxicity of green and black tea polyphenols by cobalt chloride", Toxicology Letters, Elsevier Biomedical Press, Amsterdam, NL, vol. 155, No. 1, Jan. 15, 2005.

Nagano, et al., "On-site Remediation for Unsaturated Soil Layer Using Fenton's Reagent", http://is-solution.com/library/pdf/2009/s3-18.pdf, 339-342.

International Search Report for PCT/JP2012/059453 mailed Jul. 17, 2012.

Savel, J., "Fenton reaction acceleration using maltose and ascorbic acid," *Monatsschrift für Brauwissenchaft*, (2003), vol. 56, No. 1-2, pp. 4 to 8, $2^{nd}$ paragraph of '1 Introduction', '2 Experimental procedures.

Proceedings of the $15^{th}$ Symposium on Soil and Groundwater. Contamination and Remediation, pp. 339 to 342, published in Jun. 2009, Geo-Environmental Protection Center, including a partial English-language translation thereof.

http://ww.nagasechemtex.co.jp/products/nousulsankinzokuen.pdf, Nagase Chemtex, pp. 1-13.

* cited by examiner (1)

CONTROL         SAMPLE 1
IRON(III) CHLORIDE   ASCORBIC ACID
                +
                IRON(III) CHLORIDE (2)

CONTROL         SAMPLE 2
IRON(III) CHLORIDE   SQUEEZED GRAPE
                JUICE
                +
                IRON(III) CHLORIDE (3)

CONTROL         SAMPLE 3
IRON(III) CHLORIDE   CHAFF VINEGAR
                +
                IRON(III) CHLORIDE

REACTION PRODUCT
(ASCORBIC ACID·IRON)
+
HYDROGEN PEROXIDE

ONLY HYDROGEN PEROXIDE (7)

CONTROL    SAMPLE 7
IRON(III) CHLORIDE    SQUEEZED RED
CABBAGE JUICE
+
IRON(III) CHLORIDE (8)

CONTROL    SAMPLE 8
IRON(III) CHLORIDE    SQUEEZED BANANA
JUICE
+
IRON(III) CHLORIDE (9)

CONTROL    SAMPLE 9
IRON(III) CHLORIDE    CACAO POWDER
+
IRON(III) CHLORIDE (10)

CONTROL    SAMPLE 10
IRON(III) CHLORIDE    TURMERIC POWDER
+
IRON(III) CHLORIDE

FENTON REACTION CATALYST PRODUCED USING REDUCING ORGANIC SUBSTANCE AS RAW MATERIAL

CROSS-REFERENCE TO RELATED APPLICATION

This application is a United States national phase application of International Application PCT/JP2012/059453 filed Apr. 6, 2012. Priority under 35 USC 119 is claimed based on Japanese patent application JP 2011-110173 filed May 17, 2011.

TECHNICAL FIELD

The present invention relates to a Fenton reaction catalyst. The present invention also relates to a sterilization method, a pollutant degradation method, and a luminescence method based on chemiluminescence, involving using the Fenton reaction catalyst.

BACKGROUND ART

The sterilization or removal of harmful substances is important in the agriculture and food processing field. However, many conventional methods using chemical drugs are not preferred because they could remain in foods or agricultural products. In addition, sterilization with chlorine usually results in a strong chlorine odor that is a disadvantage in this treatment.

Therefore, in the food field, ozone sterilization may be used as a sterilization method free from leaving any odor for the foods. However, this method has the disadvantage of high cost to introduce an expensive ozone gas generator in a place other than a large-scale facility.

Under such circumstances, in many industrial fields, there is a high need for development of a low cost sterilization method free from causing any harmful residual effect for human body.

Therefore, a Fenton reaction has attracted attention as a sterilization method for solving such problems.

The "Fenton reaction" refers to a reaction for generating hydroxyl radicals from hydrogen peroxide through a reaction of divalent iron. The generated hydroxyl radicals have the strongest oxidation effect among radicals.

Based on the strong oxidation effect, the reaction is expected to be applied in various fields such as sterilization and degradation of harmful substances and persistent pollutants (for example, a technology for soil cleanup by injecting a Fenton reaction catalyst into soil polluted with harmful substances).

In addition, the Fenton reaction is a technology having a low environmental burden because hydrogen peroxide is converted into harmless oxygen and water after completion of the reaction.

Hitherto, iron (II) sulfate has been generally used as a Fenton reaction catalyst. However, it is necessary to add divalent iron as needed because divalent iron is immediately oxidized to be precipitated and lose catalytic ability.

Therefore, a technology for improving solubility of ferrous sulfate using EDTA, citric acid, or the like has been developed to maintain its water solubility (see Non Patent Literature 1).

In addition, there has been reported a technology for sterilizing a mold based on the strong oxidation effect of the Fenton reaction (see Patent Literature 1).

However, in such conventional methods, there is a fatal problem in that divalent iron used as a catalyst is very unstable and cannot be prevented from being oxidized into trivalent iron, resulting in losing the catalytic ability in a short time.

Therefore, there has been required development of a stable Fenton reaction catalyst that can maintain the state of divalent iron, which is in nature unstable, for a long period of time.

Further, in the conventional Fenton reaction catalysts, trivalent iron or metallic iron, which is present in large amounts in the nature and can be inexpensively supplied, cannot be used as an iron raw material.

CITATION LIST

Patent Literature

[PTL 1] JP 2009-062350 A
[PTL 2] JP 61-59248 B

Non Patent Literature

[NPL 1] Proceedings of the 15th Symposium on Soil and Groundwater. Contamination and Remediation, p. 339-342, published in Jun. 2009, Geo-Environmental Protection Center.

SUMMARY OF INVENTION

Technical Problem

The present invention has been made in order to solve the above-mentioned problems. An object of the present invention is to develop and provide a Fenton reaction catalyst that can maintain divalent iron stably for a long period of time.

Another object of the present invention is to produce and provide a Fenton reaction catalyst that is different from a conventional Fenton reaction catalyst in the point of the possibility to use the trivalent iron or metallic iron (inexpensive iron-supplying source) by converting them to divalent iron.

Still another object of the present invention is to develop a Fenton reaction catalyst harmless to the human body and the environment.

Solution to Problem

Substances having a reducing effect (for example, ascorbic acid) can be used to reduce trivalent iron to divalent iron (see Patent Literature 2), but many of these substances have a strong radical scavenging ability (scavenger function).

Therefore, hitherto, these reductants have not been used in a Fenton reaction for generating hydroxyl radicals.

The inventors of the present invention have made intensive studies in view of such circumstances, and as a result, have found that the reaction product obtained by mixing a specific reducing organic substance (specifically ascorbic acid, a polyphenol-containing plant component, or a plant dry distillation liquid component) at a specific ratio with respect to an iron element in the presence of water has a very strong ability to catalyze the Fenton reaction.

In addition, the inventors of the present invention have found that the reducing organic substances can maintain the state of divalent iron, which is in nature unstable, stably for a long period of time, and can reduce trivalent iron into divalent iron to thereby maintain it stably for a long period of time. The inventors have also found that the reducing organic substance is acidic, and hence insoluble trivalent iron and metallic iron can be solubilized and used.

Substances having a reducing effect (for example, ascorbic acid) can be used to reduce trivalent iron to divalent iron (see Patent Literature 2), but many of these substances have a strong radical scavenging ability (scavenger function).

Therefore, hitherto, these reductants have not been used in a Fenton reaction for generating hydroxyl radicals.

The inventors of the present invention have made intensive studies in view of such circumstances, and as a result, have found that the reaction product obtained by mixing a specific reducing organic substance (specifically ascorbic acid, a polyphenol-containing plant component, or a plant distillation liquid component) at a specific ratio with respect to an iron element in the presence of water has a very strong ability to catalyze the Fenton reaction.

In addition, the inventors of the present invention have found that the reducing organic substances can maintain the state of divalent iron, which is in nature unstable, stably for a long period of time, and can reduce trivalent iron into divalent iron to thereby maintain it stably for a long period of time. The inventors have also found that the reducing organic substance is acidic, and hence insoluble trivalent iron and metallic iron can be solubilized and used.

The present invention has been made based on those findings.

That is, the present invention according to the first aspect relates to a Fenton reaction catalyst, including, as an active component, a reaction product obtained by mixing reducing organic substances with an iron-supplying source in the presence of water under any one of the following conditions (A) to (C):

(A): a condition where: the reducing organic substance is ascorbic acid; and the ascorbic acid is mixed in a molar amount 0.01 to 5 times that of an iron element supplied from the iron-supplying source;

(B): a condition where: the reducing organic substance is a reducing organic substance contained in a polyphenol-containing plant; and the polyphenol-containing plant is mixed in an amount of 0.01 to 1,000 g in terms of a polyphenol with respect to 1 mol of an iron element supplied from the iron-supplying source; and (C): a condition where: the reducing organic substance is a reducing organic substance contained in a plant dry distillation liquid; and the plant dry distillation liquid is mixed in an amount of 0.1 to 200 kg in terms of a stock solution with respect to 1 mol of an iron element supplied from the iron-supplying source.

Further, the present invention according to the second aspect relates to a Fenton reaction catalyst according to the first aspect, in which the iron-supplying source is a trivalent iron compound or metallic iron.

Further, the present invention according to the third aspect relates to a sterilization method, including using the Fenton reaction catalyst according to either the first or the second aspect to generate hydroxyl radicals from hydrogen peroxide.

Further, the present invention according to the fourth aspect relates to a pollutant degradation method, including using the Fenton reaction catalyst according to either the first or the second aspect to generate hydroxyl radicals from hydrogen peroxide.

Further, the present invention according to the fifth aspect relates to a luminescence method based on chemiluminescence, including using the Fenton reaction catalyst according to either the first or the second aspect to generate hydroxyl radicals from hydrogen peroxide.

Advantageous Effects of Invention

According to the present invention, it is possible to provide the stable Fenton reaction catalyst that can maintain divalent iron stably for a long period of time.

Further, it is possible to produce a Fenton reaction catalyst that can convert trivalent iron or metallic iron into divalent iron and can maintain the divalent iron stably for a long period of time.

As a result, it is possible to provide the Fenton reaction catalyst using an inexpensive raw material (for example, an iron compound such as iron sulfate or iron chloride, soil, or metallic iron) as an iron-supplying source.

The Fenton reaction catalyst of the present invention uses, as the reducing organic substance, ascorbic acid, a polyphenol-containing plant component, or a plant dry distillation liquid component, and is hence highly safe for the human body and the environment.

In addition, particularly in the case where a plant dry distillation liquid (by-product of carbonization) or squeezed polyphenol-containing plant juice is used as a feedstock for supplying the reducing organic substance, the Fenton reaction catalyst can be produced inexpensively.

The Fenton reaction catalyst of the present invention is expected to be used in wide range of industrial fields. For example, the catalyst can be used in food, medicine, public health, agriculture, environmental cleanup, or the like.

For example, according to the present invention, it is possible to provide the sterilization method and pollutant degradation method that are safe for the human body and the environment.

Further, according to the present invention, it is possible to provide a chemiluminescence method based on a luminol reaction or the like using the Fenton reaction catalyst. This is expected to create a novel demand as a novel luminescence method.

BRIEF DESCRIPTION OF DRAWINGS

The following figures show experimental results in the cases of using the following samples: (1): ascorbic acid; (2): squeezed grape juice; (3): chaff vinegar; (4): coffee grounds; (5): tea dregs; (6): water; (7): squeezed red cabbage juice; (8): squeezed banana juice; (9): cacao powder; and (10): turmeric powder.

DESCRIPTION OF EMBODIMENTS

Figure 1:
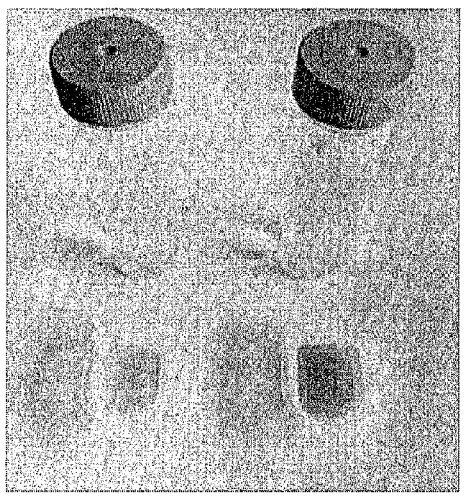
FIG. 1 are photographic images of divalent iron reduced by samples from trivalent iron and detected by using dipyridyl in Example 1. The right solution in each of the figures shows the result of an aqueous solution obtained by mixing each of the samples with iron chloride. In addition, the left solution shows the result of a solution containing only iron chloride (control).
Figure 1:
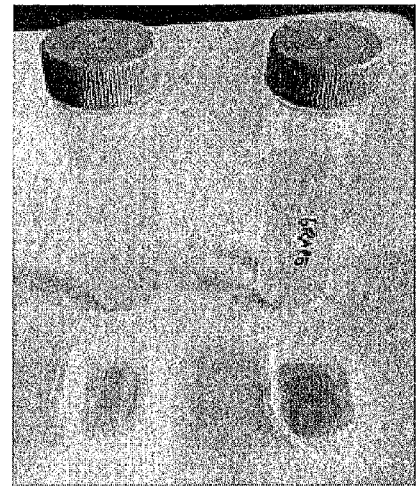
Figure 1:
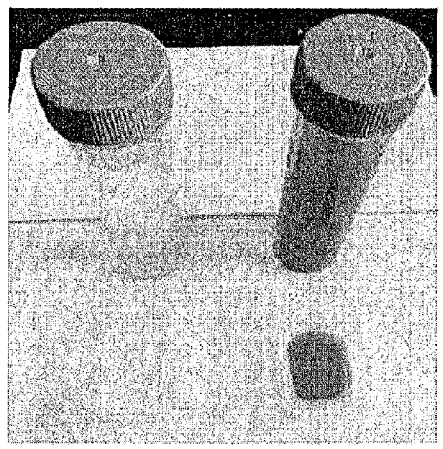

Hereinafter, embodiments of the present invention are described in detail.

The present invention relates to a Fenton reaction catalyst including, as an active component, a reaction product obtained by mixing a specific reducing organic substance at a specific ratio with respect to an iron element supplied from an iron-supplying source in the presence of water.

(Reducing Organic Substance)

The following substances (A) to (C) may be used as the reducing organic substance used for production of the Fenton reaction catalyst of the present invention. In addition, the substances may be used singly, or a mixture thereof may be used.

•(A) Ascorbic Acid

'Ascorbic acid' may be used as the reducing organic substance in the present invention.

In this case, ascorbic acid in a plant may be used as the ascorbic acid.

Ascorbic acid is considered to have both an effect of reducing trivalent iron or metallic iron into divalent iron and an effect of maintaining divalent iron stably for a long period of time.

Organs and tissues of plant which abundantly contain ascorbic acid may be used as the feedstocks for supplying ascorbic acid that may be used in the present invention.

Examples thereof may include: fruits such as a tomato, a bell pepper, an acerola, citrus fruits (such as a lemon, a lime, an orange, and a grape fruit), a persimmon, a kiwi fruit, a guava, a papaya, a blackberry, a blueberry, a strawberry, and a melon; leaves such as a parsley and a spinach; flower stalks such as a broccoli and a cauliflower; an underground stem such as a sweet potato; and a lateral bud such as a Brussels sprout.

In the present invention, the plants may be used in the form of dried plant products (in particular, powder), squeezed plant juices, or extracts (in particular, water extracts). Further, dried products of the squeezed juices or extracts may be used.

It should be noted that microbial culture product such as a koji mold may be used as the feedstocks for supplying ascorbic acid as long as the culture contains ascorbic acid at a high concentration.

In the present invention, of those, plants such as a tomato, a bell pepper, an acerola, and citrus fruits are preferably used as the feedstocks for supplying ascorbic acid, from the viewpoint of economic efficiency.

In addition, from the viewpoint of quality, purified (or partially purified) ascorbic acid is preferably added directly.

Not only free ascorbic acid but also an ascorbate compound (such as potassium ascorbate or sodium ascorbate) may be used as purified ascorbic acid.

•(B) Reducing Organic Substance Contained in Polyphenol-Containing Plant

A 'reducing organic substance contained in a polyphenol-containing plant' may be used as the reducing organic substance in the present invention.

The reducing organic substance refers to the whole of a composition including very many reducing organic substance molecules such as total polyphenols, organic acids, phenols, and carbonyls in a raw material plant.

The composition is considered to include a molecule that exhibits an effect of reducing trivalent iron or metallic iron into divalent iron, a molecule that exhibits an effect of maintaining divalent iron stably for a long period of time, and a molecule that exhibits both of the effects.

Organs and tissues of plants that abundantly contain total polyphenol used as plants that abundantly contain reducing organic substance may be used as the feedstocks for supplying the reducing organic substance.

Examples thereof can include: fruits such as a grape, a strawberry, a blueberry, a raspberry, an apple, citrus fruits (such as a lemon, a lime, an orange, and a grape fruit), a persimmon, and a banana; seeds such as a cacao, a black soybean, a black sesame, and a buckwheat; and underground stems such as a purple sweet potato and a turmeric.

In the present invention, the plants may be used in the form of dried plant products (in particular, powder), squeezed plant juices, or extracts (in particular, water extracts, alcohol extracts, or aqueous alcohol extracts). Further, dried products of the squeezed juices or extracts may be used.

It should be noted that ethanol is particularly preferably used as the alcohol used for extraction.

In the present invention, from the viewpoint of the cost of the raw material, squeezed grape juice and squeezed banana juice (juices) are preferably used.

Further, from the viewpoint of quality, extracted reducing organic substances such as total polyphenols and organic acids are preferably used as compositions.

•(C) Reducing Organic Substance Contained in Plant Dry Distillation Liquid

A 'reducing organic substance contained in a plant dry distillation liquid' may be used as the reducing organic substance in the present invention.

The reducing organic substance refers to the whole of a composition including very many reducing organic substance molecules such as organic acids, phenols, carbonyls, alcohols, amines, basic components, and other neutral components in a plant dry distillation liquid.

The composition is considered to include a molecule that exhibits an effect of reducing trivalent iron or metallic iron into divalent iron, a molecule that exhibits an effect of maintaining divalent iron stably for a long period of time, and a molecule that exhibits both of the effects.

Specifically, a stock solution, a concentrate, or a diluted solution of the plant dry distillation liquid, or a dried product thereof may be used as the feedstocks for supplying the reducing organic substance.

The plant dry distillation liquid refers to a distillation liquid obtained by thermal degradation of a plant in a reducing condition (sticky and brown liquid). The liquid has a red-brown to dark brown color.

Examples thereof include wood vinegar, bamboo vinegar, and chaff vinegar. It should be noted that, from the viewpoint of the cost of the raw material, those are preferably used.

(Iron-supplying Source)

In the present invention, any one of iron-supplying sources including a divalent iron compound, a trivalent iron compound, and metallic iron may be used as a source for supplying an iron element. Alternatively, a plurality of the iron-supplying sources may be used as a mixture.

Examples of the source for supplying divalent iron may include iron compounds such as iron (II) chloride, iron (II) nitrate, iron (II) sulfate, iron (II) hydroxide, and iron (II) oxide.

In addition, an aqueous solution obtained by dissolving any of the compounds and containing a divalent iron ion may be used.

Examples of the source for supplying trivalent iron may include: a water-soluble iron compound such as iron (III) chloride or iron (III) sulfate; an insoluble iron compound such as iron (III) oxide, iron (III) nitrate, or iron (III) hydroxide; soil such as Akadama soil, Kanuma soil, loam soil (allophanic iron-rich soil), laterite (iron (III) oxide-rich soil), or goethite (soil containing amorphous mineral); and a biogenic substance such as heme iron or seashell.

In addition, an aqueous solution obtained by dissolving a water-soluble iron compound and containing a trivalent iron ion may be used.

It should be noted that, even if the trivalent iron compound is insoluble in water, the compound may be directly used as the iron-supplying source of the present invention because the compound becomes soluble in water by the function of the reducing organic substance in the present invention showing acidity.

Examples of the source for supplying the metallic iron may include iron ore (natural iron ore such as pyrite, marcasite, siderite, magnetite, or goethite), iron sand (sand dust obtained from iron ore), and an iron material (smelted iron, alloy). Further, rust may be used as source.

It should be noted that the metallic iron is usually insoluble in water, but may be directly used as the iron-supplying source of the present invention because the metallic iron becomes soluble in water by the function of the reducing organic substance in the present invention showing acidity.

Of those, from the viewpoint of efficiently producing the Fenton reaction catalyst of the present invention, in the case where the catalyst is used in the fields of agriculture, food, medicine, and the like, an inexpensive iron compound (iron compound such as iron chloride or iron sulfate: irrespective of divalent or trivalent) is preferably used from the viewpoints of the cost of the raw material and stable supply.

Moreover, in the case where the catalyst is used in organic agriculture, a natural product of soil (in particular, Akadama soil, Kanuma soil, or allophanic loam) or metallic iron is preferably used as the iron-supplying source from the viewpoints of the necessity to limit a raw material only to a natural product as a raw material, cost of the raw material, and stable supply.

(Mixing Treatment)

In the present invention, when the feedstocks for supplying the reducing organic substance (or the reducing organic substance) is mixed with the iron-supplying source (or the iron ion) in the presence of water, a reaction product (active component) having an ability to catalyze a Fenton reaction can be obtained.

•Mixing Ratio of Raw Materials

In the present invention, when the feedstocks for supplying the reducing organic substance (or the reducing organic substance) is mixed with the iron element supplied from the iron-supplying source at a specific ratio, a reaction product having a strong ability to catalyze a Fenton reaction can be obtained.

It should be noted that, if the mixing ratio of the reducing organic substance to the iron element is too high, an excessive amount of the reducing organic substance acts as a scavenger to inhibit the Fenton reaction, which is not preferred.

In addition, if the mixing ratio of the reducing organic substance to the iron element is too low, the amount of the resultant reaction product is insufficient, which is not preferred.

(A) Specifically, in the case where the reducing organic substance is 'ascorbic acid,' it is necessary that ascorbic acid be mixed in a molar amount 0.01 to 5 times that of the iron element.

Ascorbic acid is desirably mixed in a molar amount preferably 0.02 to 2 times, more preferably 0.02 to 1 times, even more preferably 0.2 to 1 times, even more preferably about 0.5 times that of iron element.

(B) In addition, in the case where the reducing organic substance is the 'polyphenol-containing plant component,' it is necessary that the polyphenol-containing plant be mixed at a mixing ratio of 0.01 to 1,000 g in terms of a polyphenol with respect to 1 mol of the iron element.

The polyphenol-containing plant is desirably mixed in an amount of preferably 0.4 to 200 g, more preferably 10 to 100 g, even more preferably 20 to 100 g, particularly preferably about 40 g.

(C) In addition, in the case where the reducing organic substance is the 'plant dry distillation liquid component,' it is necessary that the plant dry distillation liquid be mixed at a mixing ratio of 0.1 to 200 kg in terms of a stock solution of the plant dry distillation liquid with respect to 1 mol of the iron element.

The plant dry distillation liquid is desirably mixed in an amount of preferably 0.2 to 100 kg, more preferably 20 to 100 kg, even more preferably about 50 kg.

•Mixing Procedure

The mixing procedure of the present invention is performed in the presence of water. In this case, the expression "in the presence of water" refers to a condition where the reducing organic substance can react with iron using water as a medium.

It should be noted that the amount of water may be such an amount that a solution capable of being mixed and stirred is obtained, or may be such an amount that the raw materials (reducing organic substance and iron) become wet through a mixing procedure.

It should be noted that the water may be any usual water as long as the condition allows the reaction to occur, and examples thereof may include tap water, well water, underground water, river water, deionized water, and distilled water.

It should be noted that, in the case where the squeezed plant juice or the plant dry distillation liquid is used in a liquid state as the feedstocks for supplying the reducing organic substance, the juice or the liquid may be mixed directly with the iron-supplying source for the reaction without addition of another medium.

With regard to the mixing procedure, mixing may be carried out simply by stirring, but may be carried out with a mixer, a large-scale stirring vessel, a Vortex mixer, a shaker, or the like.

In this case, the temperature of the water may be one where the water is in a liquid state (for example, 1 to 100° C.), but mixing can be carried out at about room temperature (for example, 10 to 40° C.) without particular heating.

It should be noted that, in the case where a specific natural product (specifically soil) is used as the iron-supplying source, or in the case where the iron-supplying source is mainly composed of an insoluble iron compound, it is necessary to extend the reaction time after mixing to facilitate the reaction between iron and the reducing organic substance.

In the case where heating is carried out, the upper limit is 200° C. (in the case of heating under increased pressure), but from the viewpoint of production cost, the temperature is preferably 100° C., which is the boiling point of water in usual heating, or less, more preferably 70° C. or less. It should be noted that, in order to suppress thermal degradation of the reducing organic substance under a reaction condition of 100° C. or more, it is more effective to carry out mixing in a sealed container.

With regard to a mixing time, mixing has only to be carried out for about 10 seconds or more until the reducing organic substance is brought sufficiently into contact with iron, but in order to improve uniformity, a mixing treatment is desirably carried out for 3 minutes or more.

In addition, with regard to the upper limit, in order to prevent putrescence due to propagation of microorganisms, it is desirably to make the mixing within 240 hours or less. However, in the case where a sterilization treatment is carried out, the upper limit is not particularly specified.

(Fenton Reaction Catalyst)

The reaction product (reaction product of the reducing organic substance and iron) obtained by the above-mentioned steps can maintain divalent iron stably for a long period of time, and further, has properties for converting trivalent iron or metallic iron into divalent iron to thereby maintain it stably for a long period of time.

Therefore, the reaction product obtained in the present invention may be used as the Fenton reaction catalyst in forms of a supernatant obtained after reaction or a precipitate in water-containing state without additional treatments. Further, the supernatant or the precipitate may be separated and collected respectively to be used as the Fenton reaction catalyst.

Alternatively, dried product of the supernatant and/or the precipitate (by natural drying or roasting, for example) as well as the supernatant or suspension obtained by dissolving the dried product in water may be used as the Fenton reaction catalyst.

In the case where the reaction product is used as the Fenton reaction catalyst, the concentration of the product in an aqueous solution is desirably adjusted within a certain range before use.

(A) For example, in the case of 'ascorbic acid,' when the concentration of the reaction product obtained with respect to 1 mM of an iron element added is defined as "1× standard solution," a strong ability to catalyze the Fenton reaction can be obtained at a concentration 0.05 times or more, particularly 0.1 times or more, more particularly 0.5 times or more that of the standard solution.

In particular, the desirable range of the concentration is between 0.5 and 20.0 times, more particularly between 0.5 and 10 times, even more particularly between 0.5 and 5.0 times because the catalytic ability reaches a peak.

(B) In addition, in the case of the 'polyphenol-containing plant component,' when the concentration of the reaction product obtained with respect to 1 mM of an iron element added is defined as "1× standard solution," a strong ability to catalyze the Fenton reaction can be obtained at a concentration 0.1 times or more, particularly 0.2 times or more, more particularly 1 time or more that of the standard solution.

In particular, the desirable range of the concentration is between 1 and 20.0 times, more particularly between 1 and 10 times because the catalytic ability reaches a peak.

(C) In addition, in the case of the 'plant dry distillation liquid component,' when the concentration of the reaction product obtained with respect to 1 mM of an iron element is defined as "1× standard solution," it is desired that the concentration is 0.1 to 5 times, particularly 0.2 to 5 times, more particularly about 1 time that of the standard solution because a strong ability to catalyze the Fenton reaction can be obtained.

(Use Applications)

The Fenton reaction catalyst (reaction product of the reducing organic substance and iron) of the present invention is a highly safe substance for the human body and the environment, and hence can be applicable in various fields such as medicine, food, public health, agriculture, and industry.

For example, in the case where ascorbic acid or the polyphenol-containing plant component is used as the reducing organic substance, the component is particularly expected to be used in the food field because it is a substance derived from a supplying feedstock derived from food.

It should be noted that, in the case where ascorbic acid is used as a single substance, the substance is particularly expected to be used in the food field because the substance is colorless and transparent.

In addition, in the case where the plant dry distillation liquid is used as the feedstocks for supplying the reducing organic substance, the component contains a substance having a slight odor. However, the feedstock is very inexpensive, and hence is expected to be used in the fields of, for example, agriculture, medicine, and public health.

•Sterilization Effect

The Fenton reaction catalyst of the present invention can be used in sterilization in various fields based on the property of generating hydroxyl radicals from hydrogen peroxide.

Specific examples of the object to be sterilized may include medical equipment, walls of hospital rooms, affected areas of patients, clothes, bedclothes, lines of food manufacturing equipment, food materials, kitchen goods such as a cutting board and a kitchen knife, dishes, toilet seats, handrails, farm equipment, and plants. When the above-mentioned articles are sterilized with the Fenton reaction catalyst of the present invention, the amount of hydrogen peroxide used can be significantly reduced (by about 99 to 99.9%) compared with a usual sterilization method involving using only hydrogen peroxide.

Meanwhile, in the case where the object to be sterilized includes soil, polluted water, living bodies themselves of plants, animals, microorganisms, and the like, or organisms, sterilization can be carried out using only the Fenton reaction catalyst of the present invention (without further adding hydrogen peroxide) because hydrogen peroxide derived from the organisms has already been generated in a minute amount in the object to be sterilized.

In the present invention, the sterilization is carried out in a slightly different manner for an object to be sterilized having a solid form and an object to be sterilized having a liquid form.

In the case where the object to be sterilized has a solid form, sterilization can be carried out by preparing a solution containing the Fenton reaction catalyst and hydrogen peroxide, and, for example, spraying, applying, or kneading the solution to the object to be sterilized.

It should be noted that sterilization can be carried out by immersing the object to be sterilized into the solution. Alternatively, sterilization can be carried out by applying or kneading the Fenton reaction catalyst (having a solid form) to the object to be sterilized and separately spraying hydrogen peroxide.

On the other hand, in the case where the object to be sterilized has a liquid form, sterilization can be carried out, for example, by adding, mixing the Fenton reaction catalyst (having both liquid and solid forms) and hydrogen peroxide to the object to be sterilized. It should be noted that, in the case where the Fenton reaction catalyst has a solid form, sterilization can be carried out by adding hydrogen peroxide to a liquid to be sterilized and then immersing the catalyst in it.

For the amount of the Fenton reaction catalyst used in the solution to be used in sterilization, the solution may be prepared and used at such a concentration that the ability to catalyze the Fenton reaction can be obtained. Further, the amount of hydrogen peroxide used may be a very minute amount such that about 0.1 to 20 mM may be contained in the solution.

The sterilization effect is very strong, and hence a significant sterilization effect can be exhibited by immersing the object to be sterilized for about several minutes, for example.

In the case where the Fenton reaction catalyst of the present invention is used as an active component of a sanitizer, there may be given solid and liquid forms. Specific examples thereof may include: solid forms such as powder, granule, sheet, board, cube, and sponge; and liquid forms such as a concentrate and a liquid ampoule. Examples thereof may further include a powdery form, a form of a solid mixed with an excipient or the like, a form of a capsule filled with the sanitizer, and a gel.

•Pollutant Degradation Effect

In addition, the Fenton reaction catalyst of the present invention can degrade a pollutant in polluted water or polluted soil and can be used in a step of cleanup.

In this case, examples of the polluted water may include domestic sewage, excrement water, factory effluent, and polluted river water, lake water, and seawater. Examples of the polluted soil may include soil of dump sites, industrial waste, agricultural land, and old factory site.

Further, the pollutant to be degraded specifically refers to an organic compound contained in polluted water or polluted soil in nature and examples thereof may include dioxin and PCB.

It should be noted that most of the objects to be cleaned (including a microflora) already contain a minute amount of hydrogen peroxide derived from organisms. Therefore, it is possible to degrade the pollutant by using only the Fenton reaction catalyst of the present invention (without further adding hydrogen peroxide).

In the present invention, degradation of a pollutant is carried out in a slightly different manner for an object to be cleaned having a solid form and an object to be cleaned having a liquid form.

In the case where the object to be cleaned has a solid form, degradation of a pollutant can be carried out by preparing a solution containing the Fenton reaction catalyst and hydrogen peroxide, and, for example, spraying, dispersing, applying, or kneading the solution to the object to be cleaned. It should be noted that degradation of a pollutant can be carried out by mixing and immersing the object to be cleaned into the solution. Alternatively, degradation of a pollutant can be carried out by applying or kneading the Fenton reaction catalyst (having a solid form) to the object to be cleaned and separately spraying hydrogen peroxide.

On the other hand, in the case where the object to be cleaned has a liquid form, degradation of a pollutant can be carried out by, for example, adding, mixing, spraying, or immersing the Fenton reaction catalyst (having both liquid and solid forms) and hydrogen peroxide into the object to be cleaned. It should be noted that, in the case where the Fenton reaction catalyst has a solid form, degradation of a pollutant can be carried out by adding hydrogen peroxide to a liquid to be cleaned and then immersing the catalyst in it.

For the amount of the Fenton reaction catalyst used in the solution to be used in degradation of a pollutant, the solution may be prepared and used at such a concentration that the ability to catalyze the Fenton reaction can be obtained. Further, the amount of hydrogen peroxide used may be a very minute amount such that about 0.1 to 100 mM may be contained in the solution.

The degradation effect is very strong, and hence a significant degradation effect can be exhibited by immersing the object to be cleaned for about 30 minutes, for example.

As a form in the case where the Fenton reaction catalyst of the present invention is used as an active component of the pollutant decomposer, there may be given solid and liquid forms. Specific examples thereof may include: solid forms such as powder, granule, sheet, board, cube, and sponge; and liquid forms such as a concentrate and a liquid ampoule. Examples thereof may further include a powdery form, a form of a solid mixed with an excipient or the like, a form of a capsule filled with the decomposer, and a gel.

•Luminescence Effect

Meanwhile, the Fenton reaction catalyst of the present invention can be used in luminescence based on chemiluminescence.

In this case, chemiluminescence refers to a phenomenon where a substrate is degraded by hydroxyl radicals generated by the Fenton reaction to emit light. Specific examples thereof may include chemical reactions using luminol, lophine, lucigenin, diphenyl oxalate, oxalyl chloride, and the like as luminescence substrates.

For the amount of the Fenton reaction catalyst used in the solution to be used in luminescence, the solution may be prepared and used at such a concentration that the ability to catalyze the Fenton reaction can be obtained. In addition, the amount of hydrogen peroxide used may be about 0.01 to 30,000 mM. Further, the amount of luminescence substrate may be determined suitably depending on a characteristic of each substance used (in the case of luminol, about 0.1 to 10 g/L).

The Fenton catalyst is very stable, and hence can exhibit a luminescence effect stably for a long period of time.

The luminescence reaction can be used in illumination, electrical power generation (in combination with a solar cell), or the like.

EXAMPLES

Hereinafter, the present invention is described by way of examples, but the scope of the present invention is not limited by these examples.

Example 1

Examination of Ability to Reduce Iron

An experiment on reduction of trivalent iron into divalent iron was carried out using organic substances and compositions having reducing effects.

With respect to each samples shown in Table 1, aqueous solutions were respectively prepared so that each of the solutions contained iron (III) chloride ($FeCl_3$) in the same weight (0.1% (w/v)).

It should be noted that a reagent purchased from Wako Pure Chemical Industries, Ltd. was used as 'ascorbic acid' (Sample 1).

In addition, a liquid obtained by squeezing grape with its peel (total polyphenol content: 2.3 g/L) was used as the 'squeezed grape juice' (Sample 2) (squeezed polyphenol-containing plant juice), and the concentration of the sample was adjusted based on the weight in terms of the amount of the total polyphenol contained.

Further, a stock solution of chaff vinegar extracted in production of carbonized rice husk was used as the 'chaff vinegar' (Sample 3) (plant dry distillation liquid), and the concentration of the sample was adjusted based on the liquid weight of the stock solution.

Then, each of the aqueous solutions mixed with each of the samples was allowed to stand still at room temperature for several minutes to perform a reaction. Further, an aqueous solution containing only iron chloride was prepared as a control.

0.2% dipyridyl (dipyridyl: 2 g, acetic acid: 100 g/L) was added to the aqueous solution to examine the presence or absence of a color reaction. It should be noted that dipyridyl is a substance which turns red when reacted with divalent iron and is used for detection of divalent iron. This substance does not react with trivalent iron and remains colorless.

Table 1 and FIG. 1 show the results of color development after the reaction.

The results reveal that ascorbic acid (Sample 1: FIG. 1(1)), squeezed grape juice (Sample 2: FIG. 1(2)), and chaff vinegar (Sample 3: FIG. 1(3)) have functions of reducing trivalent iron into divalent iron and can maintain the divalent iron stably.

In addition, the iron-reducing ability of chaff vinegar is considered to be attributed to reducing organic substances (organic acids, phenols, carbonyls, alcohols, amines, basic components, other neutral components) contained as components.

TABLE 1

| Sample | Reaction product | Color development |
|---|---|---|
| 1 Ascorbic acid | Ascorbic acid•iron | + |
| 2 Squeezed grape juice | Squeezed grape juice component•iron | + |
| 3 Chaff vinegar | Chaff vinegar component•iron | + |

Example 2

Examination of Ability to Catalyze Fenton Reaction

With respect to the reaction products of the samples, which were confirmed to have iron reducing effects in Example 1, and iron, the fact that the reaction products have abilities to catalyze the Fenton reaction was examined by a luminol reaction.

It should be noted that the luminol reaction means a luminescence reaction caused by oxidizing luminol by generation of hydroxyl radicals.

Small amounts of the aqueous solutions containing the reaction products prepared in Example 1 were each added to 100 ml of a luminol solution (1 g/L luminol, 4 g/L sodium hydroxide, 0.3% hydrogen peroxide), and the presence or absence of luminescence was observed.

As a result, blue fluorescence was observed in all the aqueous solutions. The results reveal that, when any of the reaction product of ascorbic acid (Sample 1) and iron, the reaction product of squeezed grape juice (Sample 2) and iron, and the reaction product of chaff vinegar (Sample 3) and iron is mixed with hydrogen peroxide, the Fenton reaction is catalyzed to generate hydroxyl radicals.

Example 3

Examination of Optimum Mixing Ratio with Iron

In the step of preparing the reaction products of the samples and iron, the ability to catalyze the Fenton reaction was examined with different mixing ratios of the samples to iron.

Figure 2:
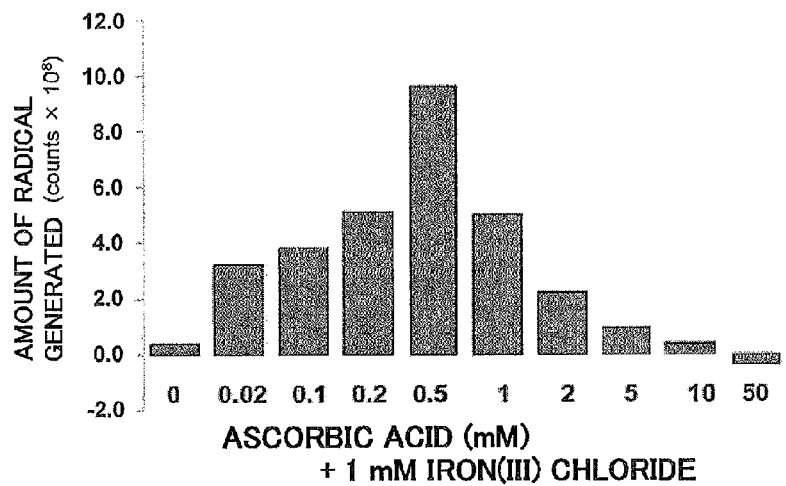
FIG. 2 are graphs showing the results of measurement of the amount of hydroxyl radicals generated by a luminol reaction using, as catalysts, reaction products obtained by mixing samples with iron at different mixing ratios in Example 3.
Figure 2:
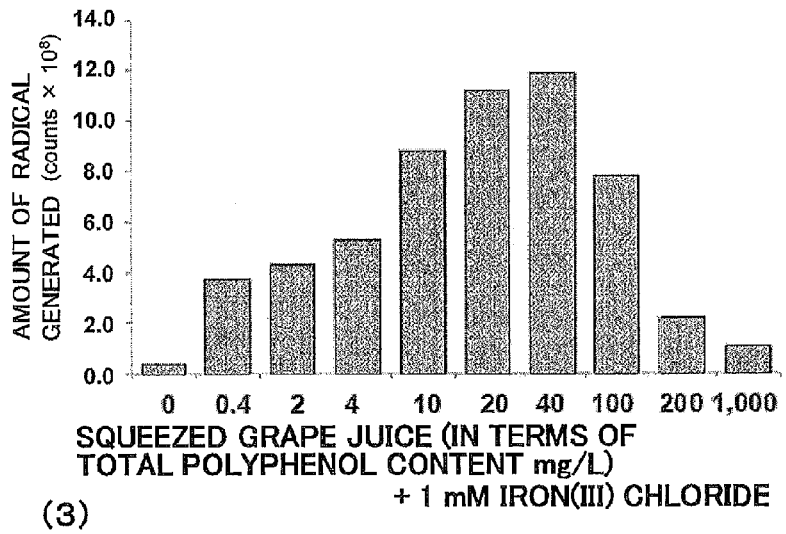
Figure 2:
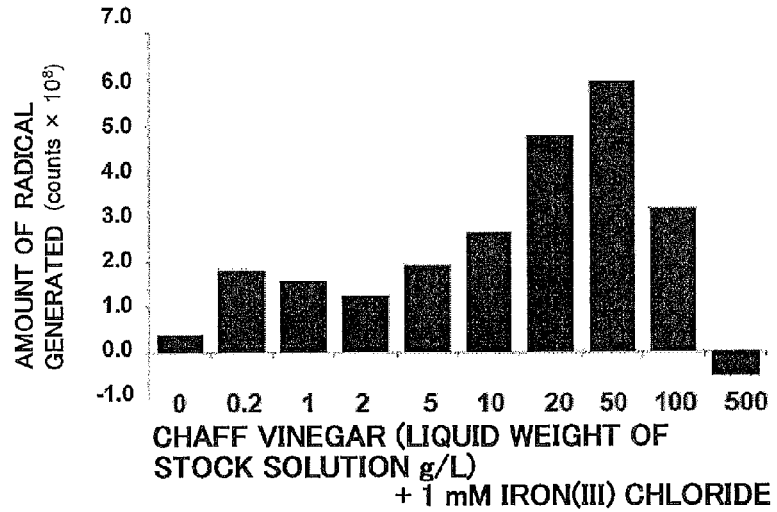

The above-mentioned samples were each mixed with iron (III) chloride (1 mM $FeCl_3$) at different mixing ratios as shown in FIG. 2 to prepare reaction products in the same manner as in Example 1.

Then, for each of the aqueous solutions containing the reaction products, the amount of luminescence (amount of hydroxyl radicals generated) provided by the luminol reaction was measured using the AB-2270 Luminescencer Octa to determine the ability of the reaction products to catalyze the Fenton reaction. FIG. 2 show the results.

i) The results reveal that a reaction product having a strong ability to catalyze the Fenton reaction can be obtained when ascorbic acid (FIG. 2 (1)) is mixed at a concentration of from 0.02 to 5 mM, particularly from 0.02 to 2 mM, more particularly from 0.02 to 1 mM, even more particularly from 0.2 to 1 mM, even more particularly about 0.5 mM with respect to 1 mM $FeCl_3$.

ii) In addition, the results reveal that a reaction product having a strong ability to catalyze the Fenton reaction can be obtained when squeezed grape juice (FIG. 2(2)) is mixed at a concentration of from 0.4 to 200 mg/L, particularly from 0.4 to 100 mg/L, more particularly from 10 to 100 mg/L, even more particularly from 20 to 100 mg/L, even more particularly about 40 mg/L in terms of total polyphenols contained in the squeezed grape juice with respect to 1 mM $FeCl_3$.

iii) In addition, the results reveal that a reaction product having a strong ability to catalyze the Fenton reaction can be obtained when chaff vinegar (FIG. 2 (3)) is mixed at a concentration of from 0.2 to 100 g/L, particularly from 10 to 100 g/L, more particularly from 20 to 100 g/L, even more particularly about 50 g/L in terms of the stock solution with respect to 1 mM $FeCl_3$.

It should be noted that the reduction in the ability to catalyze the Fenton reaction in the case where the ratio of the sample to iron is too high is considered to be caused by the radical scavenging ability of the sample.

Example 4

Examination of Optimum Concentration

The concentrations of the reaction products of the samples and iron, suitable for functioning as the Fenton reaction catalysts, were examined.

The above-mentioned samples were added to different concentrations of iron (III) chloride (0.02, 0.1, 0.2, 1, 5, and 10 mM) at the optimum mixing ratios determined in Example 3 (ascorbic acid: 0.5 mM, squeezed grape juice: 40 mg/L in terms of total polyphenols, chaff vinegar stock solution: 50 g/L, with respect to 1 mM $FeCl_3$) to prepare reaction products in the same manner as in Example 1.

Figure 3:
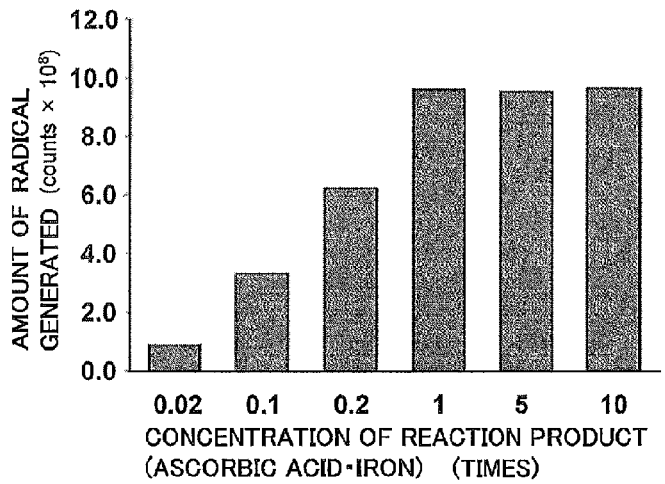
FIG. 3 are graphs showing the results of measurement of the amount of hydroxyl radicals generated by a luminol reaction using reaction products at different concentrations in Example 4.
Figure 3:
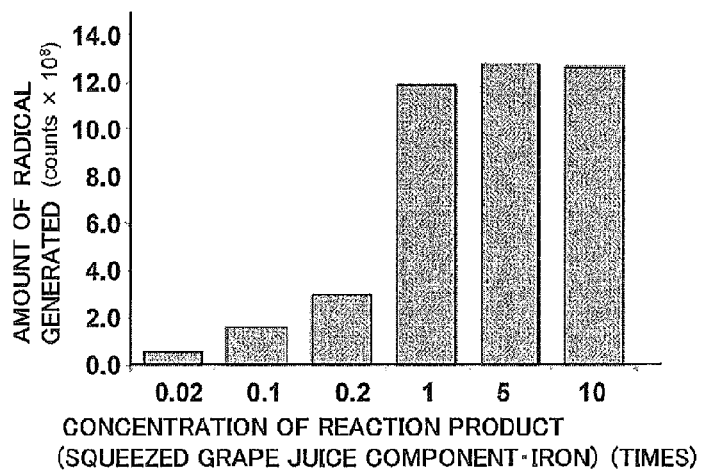
Figure 3:
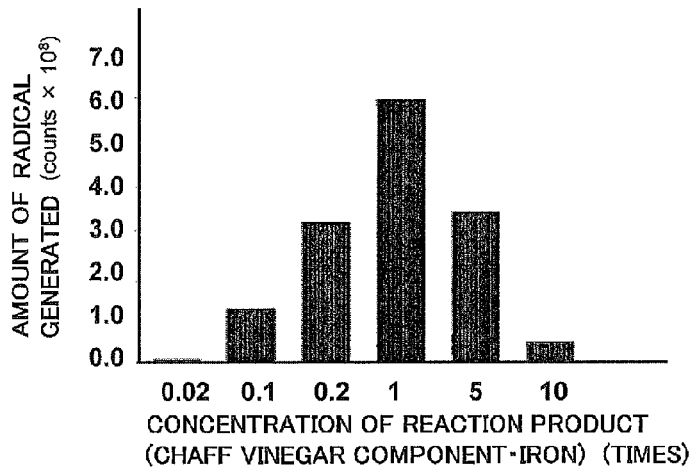

Then, for each of the aqueous solutions containing the reaction products, the amount of luminescence (amount of hydroxyl radicals generated) provided by the luminol reaction was measured using the AB-2270 Luminescencer Octa to determine the ability of the reaction products to catalyze the Fenton reaction. FIG. 3 show the results.

It should be noted that, in FIG. 3, the concentration of each reaction product (horizontal axis) represents a multiplying factor in the case where the concentration of a reaction product obtained when the concentration of iron (III) chloride added is 1 mM is defined as "1× standard solution."

i) The results reveal that a strong ability to catalyze the Fenton reaction can be obtained when the concentration of the reaction product of ascorbic acid and iron (FIG. 3(1): ascorbic acid•iron) is 0.1 times or more, particularly 0.2 times or more, more particularly 1 time or more. In particular, the results reveal that the concentration reaches a peak in a range of from 1 to 10 times.

ii) In addition, the results reveal that a strong ability to catalyze the Fenton reaction can be obtained when the concentration of the reaction product of squeezed grape juice and iron (FIG. 3(2): squeezed grape juice component•iron) is 0.1 times or more, particularly 0.2 times or more, more particularly 1 time or more. In particular, the results reveal that the concentration reaches a peak in a range of from 1 to 10 times.

iii) In addition, the results reveal that a strong ability to catalyze the Fenton reaction can be obtained when the concentration of the reaction product of chaff vinegar and iron (FIG. 3(3): chaff vinegar component•iron) is 0.1 to 5 times, particularly 0.2 to 5 times, more particularly about 1 time.

It should be noted that the reduction in the ability to catalyze the Fenton reaction in the case where the concentration of the reaction product is too high is considered to be caused by the presence of a substance having a radical scavenging ability in the chaff vinegar component.

Example 5

Comparison of Abilities to Catalyze Fenton Reaction

The abilities of the reaction products of various samples and iron to catalyze the Fenton reaction were compared.

Respective aqueous solutions containing the reaction product of ascorbic acid (Sample 1) and iron, the reaction product of squeezed grape juice (Sample 2) and iron, and the reaction product of chaff vinegar (Sample 3) and iron were prepared at the optimum mixing ratios and the optimum concentrations determined in Examples 3 and 4 in the same manner as in Example 1.

In addition, coffee grounds (Sample 4) and tea dregs (Sample 5) described in Specification of Japanese Patent Application No. 2010-080605 (application relating to a Fenton reaction catalyst by the inventors of the present application) were respectively added at a sample concentration of 4 g/L with respect to 1 mM iron (III) chloride to prepare aqueous solutions containing reaction products of the samples and iron. The preparation was carried out in the same manner as in Example 1.

Further, an aqueous solution containing only water (Sample 6) and 1 mM iron (III) chloride was prepared as a comparative control.

It should be noted that aqueous solutions containing only the samples (Fe-free aqueous solutions) were prepared as controls for the above-mentioned respective aqueous solutions.

Figure 4:
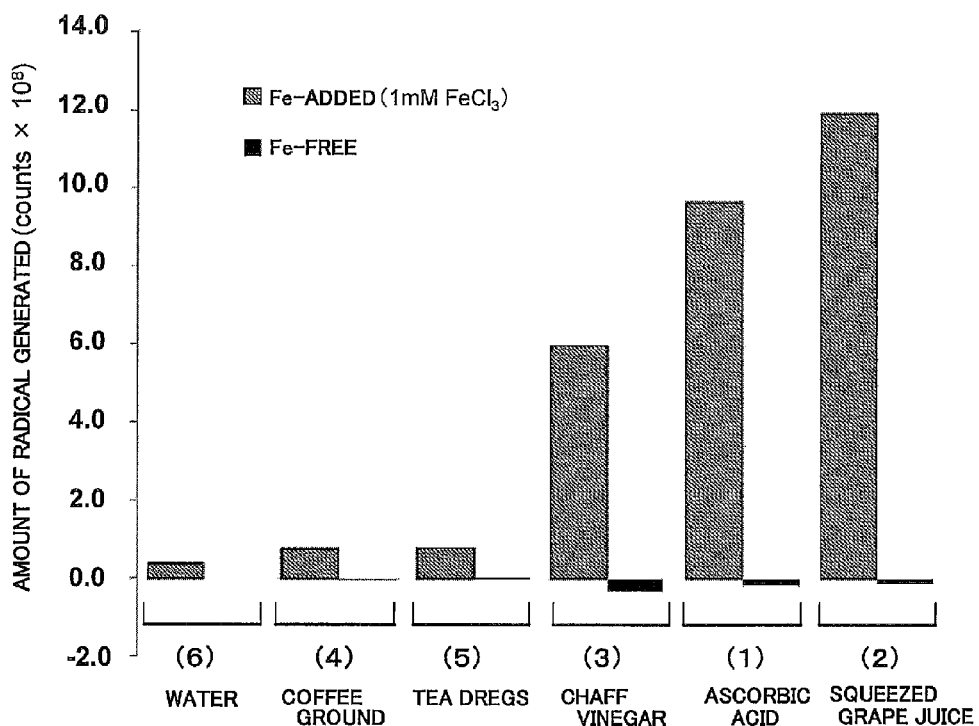
FIG. 4 is a graph showing the results of measurement of the amount of hydroxyl radicals generated by a luminol reaction using, as catalysts, reaction products of samples and iron in Example 5. The left measurement result of each of treatment groups shows the result of a mixture of each of the samples and iron chloride. In addition, the right measurement result shows the result of a solution containing each of the samples alone (control).

Then, for each of the aqueous solutions, the amount of luminescence (amount of hydroxyl radicals generated) provided by the luminol reaction was measured using the AB-2270 Luminescencer Octa to determine the ability of the reaction products to catalyze the Fenton reaction. FIG. 4 shows the results.

The results reveal that the respective reaction products of ascorbic acid, squeezed grape juice, and chaff vinegar and iron have very high abilities to catalyze the Fenton reaction (Samples 1 to 3).

In particular, the reaction product of the squeezed grape juice (Sample 2) and iron was found to have a catalytic ability about 20 times as high as that of the reaction product of the coffee grounds (Sample 4) and iron or the reaction product of the tea dregs (Sample 5) and iron.

Example 6

Sterilization Effect

The sterilization effect of the Fenton reaction using the reaction product of ascorbic acid and iron was examined for *Escherichia coli*.

A reaction product was obtained in the same manner as in Example 1 so that the product contained ascorbic acid at a concentration of 10 mM with respect to iron (III) chloride (10 mM $FeCl_3$).

Hydrogen peroxide was added at a concentration of 10 mM to an aqueous solution containing the reaction product (10 mM ascorbic acid•iron), and *Escherichia coli* was added thereto at a density of $1.0 \times 10^6$ cfu/mL.

It should be noted that, as a control, *Escherichia coli* was added to an aqueous solution containing only hydrogen peroxide (10 mM) in the same way as above to prepare a sample.

Figure 5:
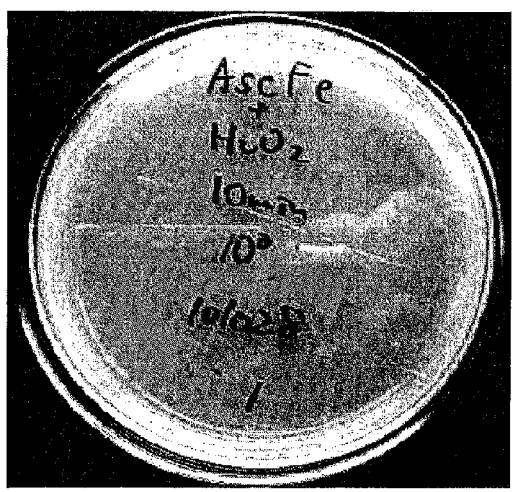
FIG. 5 are photographic images showing a sterilization effect by a Fenton reaction catalyzed by a reaction product in Example 6. (1): A photographic image showing a sterilization effect of ascorbic acid•iron+hydrogen peroxide. (N): A photographic image showing a sterilization effect of only hydrogen peroxide (control).
Figure 5:
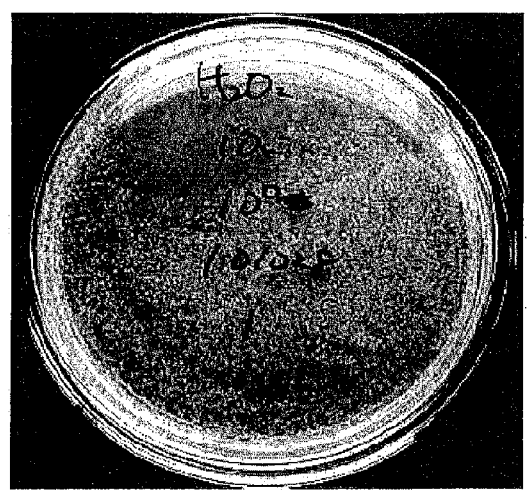

Then, 10 minutes later, 0.1 mL of each of the solutions was put on a TTC medium plate. FIG. 5 show the results.

As a result, *Escherichia coli* treated by adding the reaction product (ascorbic acid•iron) and hydrogen peroxide (FIG. 5(1)) completely died by a 10 minutes of treatment. On the other hand, in the case of the treatment using only hydrogen peroxide, a large amount of *Escherichia coli* survived (FIG. 5(N)).

This shows that, when the reaction product of ascorbic acid and iron is mixed with hydrogen peroxide, the Fenton reaction can be catalyzed to exhibit a strong sterilization effect.

Example 7

Examination of Ability to Reduce Iron in other Polyphenol-Containing Plant Extracts The abilities to reduce iron of samples derived from polyphenol-containing plants other than the squeezed grape juice (Sample 2) were examined by the dipyridyl reaction.

Aqueous solutions were respectively prepared by blending each of Samples 7 to 10 shown in Table 2 with 1 mM iron (III) chloride. Then, each of the mixed aqueous solutions was allowed to stand still at room temperature for several minutes to perform a reaction.

Figure 6:
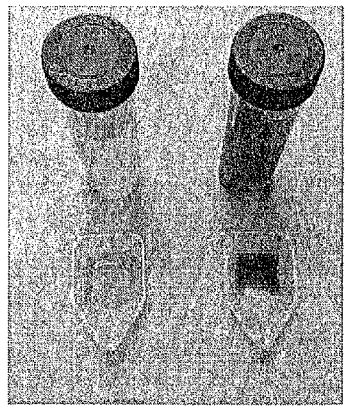
FIG. 6 are photographic images of divalent iron reduced by samples from trivalent iron and detected by dipyridyl in Example 7. The right solution in each of the figures shows the result of an aqueous solution obtained by mixing each of the samples with iron chloride. In addition, the left solution shows the result of a solution containing iron chloride alone (control).
Figure 6:
Figure 6:
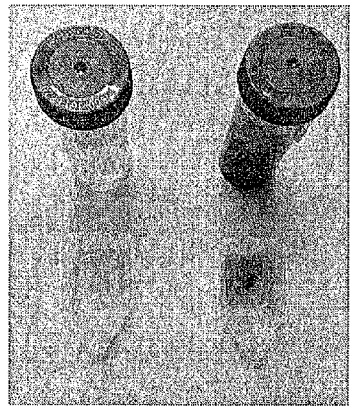
Figure 6:
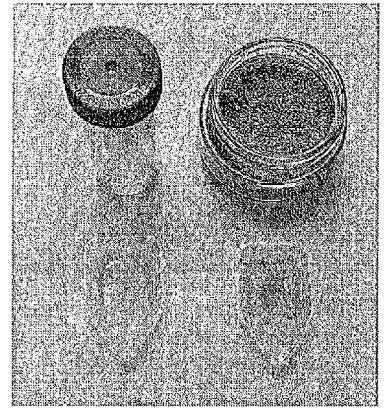

The prepared aqueous solutions were reacted with dipyridyl in the same manner as in Example 1. Table 2 and FIG. 6 show the results.

The results reveal that all of squeezed red cabbage juice (Sample 7: FIG. 6(7)), squeezed banana juice (Sample 8: FIG. 6(8)), cacao powder (Sample 9: FIG. 6(9)), and turmeric powder (Sample 10: FIG. 6(10)) have ability to reduce trivalent iron into divalent iron and maintain the divalent iron stably.

This confirms that many polyphenol-containing plants include components having activities to reduce iron.

TABLE 2

| Sample | Reaction product | Color development |
|---|---|---|
| 7 Squeezed red cabbage juice | Squeezed red cabbage juice component•iron | + |
| 8 Squeezed banana juice | Squeezed banana juice component•iron | + |

TABLE 2-continued

| Sample | Reaction product | Color development |
|---|---|---|
| 9 Cacao powder | Cacao component•iron | + |
| 10 Turmeric powder | Turmeric component•iron | + |

Industrial Applicability

The Fenton reaction catalyst of the present invention is expected to be used in wide industrial fields because all raw materials of the catalyst are easily available and are safe for the human body and the environment.

The catalyst is expected to be used in sterilization in the fields of agriculture, food, medicine, and public health, for example. Further, the catalyst is also expected to be used in a pollutant degradation method. In addition, when the catalyst is combined with a reaction with a chemiluminescence substance, the catalyst is expected to create a new demand as a novel luminescence method.

The invention claimed is:

1. A Fenton reaction catalyst, comprising, as an active component, a reaction product obtained by mixing reducing organic substances with an iron-supplying source in the presence of water under any one of the following conditions (A) to (C):

(A): a condition where the reducing organic substance is ascorbic acid; and the ascorbic acid is mixed in a molar amount of 0.5 to 5 times that of an iron element supplied from the iron-supplying source;

(B): a condition where the reducing organic substance is a composition including reducing organic substance molecules contained in a polyphenol-containing plant; and the polyphenol-containing plant is mixed in an amount of 0.01 to 1,000 g in terms of a polyphenol with respect to 1 mol of an iron element supplied from the iron-supplying source; and (C): a condition where the reducing organic substance is a composition including reducing organic substance molecules contained in a plant dry distillation liquid; and the plant dry distillation liquid is mixed in an amount of 0.1 to 200 kg in terms of a stock solution with respect to 1 mol of an iron element supplied from the iron-supplying source.

2. The Fenton reaction catalyst according to claim 1, wherein the iron-supplying source is a trivalent iron compound or metallic iron.

3. A sterilization method, comprising using the Fenton reaction catalyst according to claim 2 to generate hydroxyl radicals from hydrogen peroxide.

4. A pollutant degradation method, comprising using the Fenton reaction catalyst according to claim 2 to generate hydroxyl radicals from hydrogen peroxide.

5. A light emission method based on chemiluminescence, comprising using the Fenton reaction catalyst according to claim 2 to generate hydroxyl radicals from hydrogen peroxide.

6. A sterilization method, comprising using the Fenton reaction catalyst according to claim 1 to generate hydroxyl radicals from hydrogen peroxide.

7. A pollutant degradation method, comprising using the Fenton reaction catalyst according to claim 1 to generate hydroxyl radicals from hydrogen peroxide.

8. A light emission method based on chemiluminescence, comprising using the Fenton reaction catalyst according to claim 1 to generate hydroxyl radicals from hydrogen peroxide.

* * * * *